United States Patent [19]

Bradley

[11] Patent Number: 4,584,888
[45] Date of Patent: Apr. 29, 1986

[54] APPARATUS FOR SAMPLING FLUID FLOW

[75] Inventor: Norman Bradley, Culcheth, England

[73] Assignee: National Nuclear Corporation Limited, London, England

[21] Appl. No.: 645,269

[22] Filed: Aug. 29, 1984

[30] Foreign Application Priority Data

Sep. 15, 1983 [GB] United Kingdom ............... 8324727

[51] Int. Cl.⁴ .............................................. G01N 1/16
[52] U.S. Cl. ............................. 73/863.82; 73/863.86; 73/863.33
[58] Field of Search ........... 73/863.31, 863.33, 863.82, 73/863.86

[56] References Cited

U.S. PATENT DOCUMENTS 3,757,583  9/1973  Ludwig, Jr. ..................... 73/863.33
4,462,265  7/1984  Rein ................................ 73/863.33

FOREIGN PATENT DOCUMENTS 2064764  6/1981  United Kingdom ............ 73/863.31
2096520  10/1982  United Kingdom .

215591  4/1968  U.S.S.R. ......................... 73/863.33

OTHER PUBLICATIONS

"An Automated Multisample Stream Chemical Monitoring System", *American Laboratory;* vol. 9, No. 2; Feb. 1977; pp. 47-48, 50, 52; Heinz P. Kollig.

*Primary Examiner*—Stewart J. Levy
*Assistant Examiner*—Tom Noland
*Attorney, Agent, or Firm*—William R. Hinds

[57] ABSTRACT

Apparatus for sampling fluid flow in a plurality of passages comprises a conduit connected to the passages. A device is movable along the conduit to connect a selected passage to the conduit and allow flow from the passage through the device and conduit to test equipment which may be external to a vessel containing the passages. In one arrangement normally-closed valves are associated respectively with the passages and the movable device opens the valve of the selected passage. In an alternative arrangement which obviates the need for valves, a flexible pipe in the conduit may be used to pull the device, the flow being along the pipe.

10 Claims, 3 Drawing Figures

APPARATUS FOR SAMPLING FLUID FLOW

BACKGROUND OF THE INVENTION

This invention relates to apparatus for sampling fluid flow.

In a matrix of channels, each having individual flow conditions, within a vessel, it is often necessary to know one or more of the composition, contamination, temperature, pressure of the fluid flow. With small groups of channels it is possible to check an individual sample line from each channel, but in a large matrix space restrictions preclude this solution. Neither is it possible to obtain sensitive detection of contamination if the contaminants are subject to plate-out on the sample lines.

FEATURES AND ASPECTS OF THE INVENTION

According to this invention apparatus for sampling fluid flow in a plurality of passages comprises a conduit, respective flow connections between the passages and the conduit, a device in the conduit having spaced seals engageable with the conduit, there being means enabling flow from the space between said seals along the conduit, and means for moving the device along the conduit to communicate the flow connection of a selected passage with the space between the seals.

The moving means may be hollow and the flow from said space along the conduit may comprise flow through the hollow moving means.

The apparatus may comprise normally-closed valves respectively associated with the flow connections, said device including means engageable with a respective valve to open the valve to permit flow from the flow connection to said space.

The moving means may comprise a flexible member and the flow from said space is outside said member.

The device may comprise an apertured member between mountings including said seals.

There may be filter means in the device for flow through said space.

The passages may be in a vessel and the conduit may have two ends extending through a wall of the vessel.

DESCRIPTION OF THE DRAWINGS

The invention may be performed in various ways and two specific embodiments with possible modifications will now be described by way of example with reference to the accompanying somewhat diagrammatic drawings, in which.

DESCRIPTION OF PREFERRED EMBODIMENTS

Figure 1:
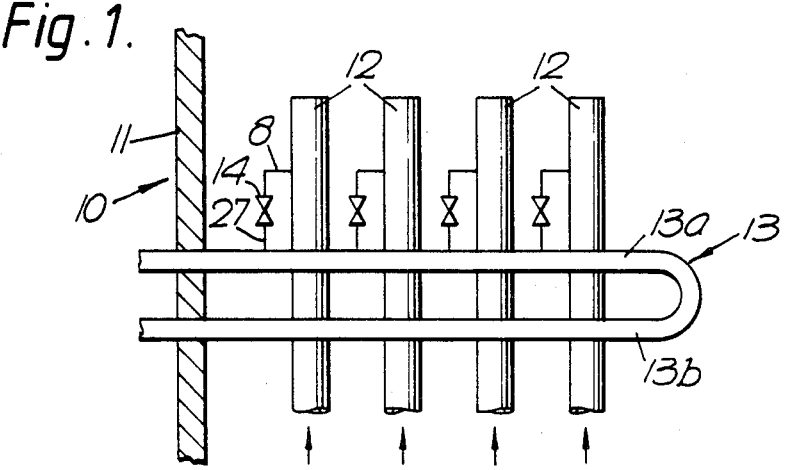
FIG. 1 illustrates a sampling arrangement for a matrix of channels.

Referring to FIG. 1, a vessel 10, only one wall 11 of which is shown, contains a matrix of channels 12 (only four shown) through which in use a fluid flows for example upwards as shown. The fluid may be liquid or gas, or have particulates suspended in the liquid or gas.

A conduit 13 is connected by individual valves 14 to the respective channels 12. The conduit 13 extends in sealed manner through the wall 11 to test equipment (not shown) outside the vessel. The conduit 13 is typically U-shaped having two arms 13a, 13b extending through the wall 11.

The valves 14 are normally closed so that none of the fluid flow in the channels passes to the conduit 13. To sample the flow in a selected channel, a sampler plug is drawn through the conduit to open the valve associated with the selected channel.

Figure 2:
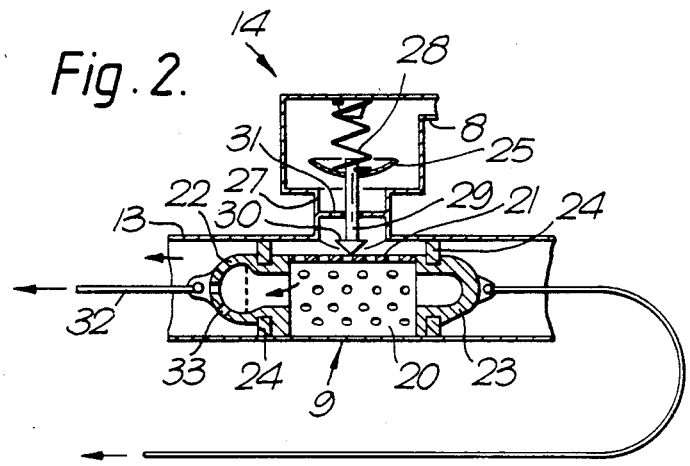
FIG. 2 is a longitudinal section through one sampler.

One suitable sampler plug 9 is shown in FIG. 2 and comprises a perforated cylinder 20 of which part 21 is shown in section. The cylinder 20 is sealingly mounted in flexible end mountings 22, 23 each of which support annular brush seal 24 which seals against the inner surface of conduit 13. Each valve 14 includes a valve member 25 normally sealing against a valve seat formed by the end of passage 27. The valve member 25 is biassed by spring 28 into engagement with the valve seat and is fixed to stem 29 having a curved head 30 and slidingly guided in annular element 31. When the plug 9 is pulled into position using flexible chain or cable 32, the cylinder 20 engages head 30 and opens the valve. Fluid from channel 12 can then flow into the valve through passage 8 and then into the cylinder 20 and through apertures 33 in end mounting 22 into conduit 13a and thence to the test equipment. When the test is finished, the plug is moved away from the channel and the valve 14 closes.

Figure 3:
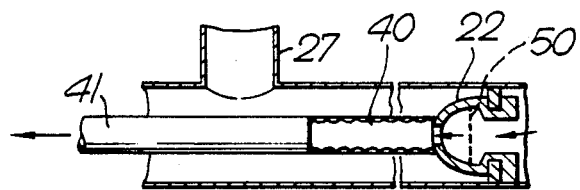
FIG. 3 is a view similar to FIG. 2 of part of a modified sampler.

In the modified plug of FIG. 3, which is generally the same as that of FIG. 2, so only a part is shown, the cable 32 takes the form of a flexible corrugated pipe 40 having a braided wire covering sheath 41. In this case the sample fluid flows through the pipe 40. The valves 14 are omitted in this arrangement. The plug 9 is moved so that the passage 27 of a selected channel is between brush seals so that flow through pipe 40 is only from the selected channel.

In either of the plugs, a filter 50 can be included in the end mounting 22, for example by a screw thread connection, to give improved sensitivity.

One example of use of the sampler is in the dry storage of radioactive material. British Patent Specification No. 2096520 shows a dry fuel store with 625 channels each holding a sealed container filled with irradiated fuel. The fuel is cooled by a passage of air over the container and through the channel, with the conditions in each channel varying according to the fuel rating. It is desirable to check the temperature in each channel to confirm that an acceptable rated fuel container is present and to monitor the decay heat rating. Should the container barrier leak, it is desirable to locate the leaking container so that it may be removed to prevent any contamination of the cooling circuit. With the present invention a single sample line 13 between rows of 25 channels may be connected to sampling equipment external to the container vessel. The plug 9 is drawn through the sample line by cable or chain, and as it reaches each channel that channel is connected into the sample line. Contamination in the form of air or waterborne particulates will collect on the filter and will be separated from the fluid flow and the plug 9 can be withdrawn carrying the filter with it. The contamination can then be measured outside the container vessel. Where maximum sensitivity is required the filter is screwed into the actuator plug and the plug moved to the desired location where it remains for the necessary sampling time. It is then removed for monitoring outside the container vessel.

I claim:

1. Apparatus for sampling fluid flow in a plurality of passages comprising a conduit, respective flow connections between the passages and the conduit at axially spaced points along the conduit, a device in the conduit having spaced seals engageable with the conduit at axially spaced positions, there being means enabling flow from the space between said seals along the conduit and means for moving the device axially along the conduit to communicate the flow connection of a selected passage with the space between the seals, whereby axial movement of the device enables communication between different passages and said space, and hence along the conduit, to be established at will.

2. Apparatus as claimed in claim 1, in which the moving means is hollow and the flow from said space along the conduit comprises flow through the hollow moving means.

3. Apparatus as claimed in claim 1, including normally closed valves respectively associated with the flow connections, said device including means engageable with a respective valve to open the valve to permit flow from the flow connection to said space.

4. Apparatus as claimed in claim 3, in which the moving means comprises a flexible member and the flow from said space is outside said member and within the conduit.

5. Apparatus as claimed in claim 1, in which the device comprises an apertured member between mountings including said seals.

6. Apparatus as claimed in claim 1, comprising filter means in the device for flow through said space.

7. Apparatus as claimed in claim 1, in which the passages are in a vessel and the conduit has two ends extending through a wall of the vessel, said moving means being accessible from each of said ends.

8. Apparatus for sampling fluid flow in a plurality of passages, said apparatus comprising a conduit, respective flow connections between the passages and the conduit, said flow connections being spaced apart longitudinally of the conduit; a device slidably received in said conduit and arranged to make sealing engagement with the conduit at spaced positions whereby a chamber is defined between the seal positions; means for moving the device along the conduit to bring the chamber into registry, one at a time, with said flow connections and means affording communication between a said passage with which the chamber is in registry and a remote location while isolating that passage from the other passages.

9. Apparatus as claimed in claim 8 in which said moving means include lengths of cable, chain or like flexible elements connected to said device and extending to opposite ends of said conduit.

10. Apparatus as claimed in claim 8 in which said moving means includes a hollow member extending from said device and out of one end of said conduit, the hollow member constituting said communication-affording means whereby fluid emanating from a said passage via said chamber is conducted along the conduit to said remote location without intermingling with fluid from the other passages as it passes along the hollow member.

* * * * *